United States Patent [19]

Lee

[11] 4,052,333

[45] Oct. 4, 1977

[54] CATALYST TREATMENT

[75] Inventor: Emerson H. Lee, Creve Coeur, Mo.

[73] Assignee: Monsanto Company, St. Louis, Mo.

[21] Appl. No.: 699,779

[22] Filed: June 25, 1976

[51] Int. Cl.$^2$ .......................................... B01J 23/92
[52] U.S. Cl. ..................................... 252/416; 252/420; 252/437; 252/456; 260/465.3
[58] Field of Search ....................... 252/416, 420, 437; 260/465.3

[56] References Cited

U.S. PATENT DOCUMENTS

| | | | |
|---|---|---|---|
| 3,642,930 | 2/1972 | Grasseli et al. | 260/465.3 |
| 3,691,224 | 9/1972 | Caporali | 260/465.3 |
| 3,746,657 | 7/1973 | Miller et al. | 252/437 |
| 3,882,159 | 5/1975 | Callahan et al. | 260/465.3 |
| 3,883,573 | 5/1975 | Milberger et al. | 260/465.3 |

*Primary Examiner*—Winston A. Douglas
*Assistant Examiner*—P. E. Konopka
*Attorney, Agent, or Firm*—J. C. Logomasini; P. L. Passley; S. M. Tarter

[57] ABSTRACT

A process for the regeneration of a spent molybdenum-containing ammoxidation catalyst which comprises heating the catalyst at atmospheric pressure or higher and at 400° C or higher for at least 1 hour in an atmosphere comprising 20–45% by volume of steam, the balance being air or a gas inert to the catalyst under the above conditions.

5 Claims, No Drawings

CATALYST TREATMENT

BACKGROUND OF THE INVENTION

This invention relates to a process for improving the effectiveness of a catalyst composition. More specifically this invention relates to a process for improving the productivity of a molybdenum-based catalyst by an improved regeneration operation.

The method used to regenerate catalysts depends to a great extend on the reaction for which it is a catalyst since it is the actual use in the reaction which causes de-activation. Thus regeneration methods of use with catalysts used in an alkylation reaction for example would not be expected to be effective in regenerating an ammoxidation catalyst.

Most catalysts used in ammoxidation processes are found not to maintain a uniform level of activity in use but to drop off in effectiveness after a number of days use. The catalyst is at that stage designated at "spent". It has been found possible to restore a substantial proportion of the activity of many such spent catalysts by a simple regeneration process. Most commonly this involves simply heating the spent catalyst in air at an elevated temperature, for example for 300° to 900° C or perhaps even higher. The temperature and time of heating are generally selected to minimize any side effects on the inert substrate upon which such catalysts are conventionally supported.

One regeneration method for such catalysts is disclosed in Def. Pub. No. T784,946. In the document the method described involves heating the deactivated catalyst at a high temperature (350°-650° C is declared appropriate) with a reducing gas or gaseous mixture.

The more common approach, however, is to use a non-reducing atmosphere, such as dry air, as is used in the regeneration apparatus described in U.S. Pat. No. 3,141,742.

In U.S. Pat. No. 3,882,159 a method of regenerating molybdena-containing catalysts is described which comprises heating spent catalyst in a fluidized bed in the presence of fluidized particles comprising molybdena and an inert support. The heating is conducted in air and steam which is said to facilitate the transfer of molybdena to the spent catalyst particles from the fluidized particles.

The present invention provides a process for regenerating the activity of a spent molybdenum-containing ammoxidation catalyst which does not depend on the addition of a further catalyst component.

The process of the invention has the advantage that the yield of the desired product based on the ammonia and olefin starting materials, is significantly increased. In an area where a yield improvement of a single percentage point can mean an increase in profitability of a plant in the order of several hundred thousand dollars over a full year, the enhanced performance of the catalysts that have been subjected to the process of the invention is regarded as extremely significant. A further advantage is that the catalysts so regenerated appear to have increased stability and a decreased tendency to burn ammonia when used in an ammoxidation reaction.

The process of the present invention results in a catalyst with a slightly decreased activity (as reflected by conversion) but a greater selectivity (such that the efficiency of the overall ammoxidation process is increased) by comparison with conventionally regenerated catalysts, especially when used in ammoxidation reactions operated under superatmospheric pressures.

SUMMARY OF THE INVENTION

The present invention provides a process for the regeneration of spent ammoxidation catalyst in which at least 20% of the atoms of the active metallic elements in the catalyst are molybdenum atoms which comprises heating the spent catalyst at a temperature of at least 400° C. and at a pressure of from 1.0 to 2.5 kg/cm$^2$ in an atmosphere comprising from 20 to 45% by volume of steam, the balance being air or a gas inert to the catalyst under the above conditions for a period of at least 1 hour such as from 1 to 24 hours and preferably from 1–4 hours.

The temperature at which the catalyst is heated is above 400° C but in practice there is often also an upper limit of about 650° C since higher temperatures do not necessarily produce results either more rapidly or to a greater degree. In fact, too high a temperature can damage the coherence of the catalyst especially where the active catalytic components are supported on an inert substrate. The temperatures used in the process of the reaction is therefore preferably in the range 400° to 650° C and most commonly 500° to 550° C.

The regeneration of the ammoxidation catalyst is conveniently conducted about atmospheric pressure or a pressure that may be a little above atmospheric. The present invention also is most conveniently conducted at or above atmospheric pressure and the actual pressure used in practice is usually from 1.0 to 2.0 kg.sq.cm.

Thus the temperature and pressure used in the process of the reaction are those which characterize conventional regeneration processes. The present process however is distinct from such processes in that the atmosphere in which it is carried out comprises from 20 to 45% by volume of steam and preferably 30 to 40% by volume. At about atmospheric pressure the preferred partial pressure of steam in the gaseous atmosphere is from 200–300 mm. The balance of the gaseous atmosphere can be provided by oxygen, air or some suitable inert gas such as helium, argon or nitrogen. The gas most convenient for the reaction is however air which has the considerably advantage of being cheap and readily available.

The catalyst which is regenerated by the process of the reaction is one in which at least 20% and preferably 40 or 50% of the active metallic atoms in the ammoxidation catalyst are molybdenum. This does not of course include metal atoms in any inert substrate upon which the active catalytic components may be supported. Other metallic elements that can be present in the catalyst include iron, potassium, bismuth, tungsten, nickel, cobalt, antimony, uranium, vanadium, titanium, copper, zinc, chromium, and thallium. Typical catalysts that can be enhanced by the process of the reaction include those described in the Examples of U.S. Pat. Nos. 3,766,092, 3,778,386, 3,471,556, 3,446,840 and 3,642,930.

The catalyst itself is most frequently supported on an inert substrate such as silica, alumina, or silica/alumina. The substrate can form up to 90% of the total catalyst weight and preferably from 40 to 60% of the total catalyst weight.

While the invention has proved extremely useful in the regeneration of spent catalyst it can often also produce good results when used to calcine new catalysts in place of the traditional air-calcination.

SPECIFIC EMBODIMENTS

The invention is further illustrated by reference to the following Examples:

In the first Example, an ammoxidation catalyst of the type described in Example 1 of U.S. Pat. No. 3,882,159 was used in an ammoxidation process for an extended period. The catalyst was tested for efficiency in an ammoxidation reaction when fresh, after a protracted period of use and after regeneration by the process of the invention.

In the second Example the performance of some catalyst at plant-conditioned peak performance state is compared with its performance when regenerated by the conventional air heating and by the process of the invention.

In both Examples, the catalyst regenerated by the process of the invention shows a distinct improvement in performance especially as regards selectivity and yield.

In what follows, reference is made to certain terms by which the performance of the catalyst is measured. The significance of those terms is as follows:

$$\% \text{ Conversion:} = \frac{\text{Mols } C_3H_6 \text{ in feed} - \text{Mols of } C_3H_6 \text{ in effluent}}{\text{Mols } C_3H_6 \text{ in Feed}} \times 100$$

$$\% \text{ Selectivity:} = \frac{\text{Mols acrylonitrile in effluent}}{\text{Mols } C_3H_6 \text{ converted}} \times 100$$

$$\% \ C_3\text{-}H_6 \text{ Yield} = \frac{\text{Mols acrylonitrile in effluent}}{\text{Mols } C_3H_6 \text{ in feed}} \times 100$$

$$\% \ NH_3 \text{ Yield:} = \frac{\text{Mols acrylonitrile in effluent}}{\text{Mols } NH_3 \text{ in feed}} \times 100$$

$$[\text{NB } \% \text{ Yield} = \frac{\% \text{ Selectivity} \times \% \text{ Conversion}}{100}]$$

These Examples describe the performance of a catalyst composition in which the catalytic elements are in the following atomic ratio:

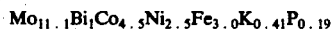

$Mo_{11.1}Bi_1Co_{4.5}Ni_{2.5}Fe_{3.0}K_{0.41}P_{0.19}$

The catalyst is supported on silica such that the silica represents 50 percent by weight of the total weight of the catalyst composition.

EXAMPLE 1

This Example illustrates the improvement in the performance of a degenerated catalyst that had been used for a protracted period in an ammoxidation reaction after treatment by the process of the invention. For comparison the performance of the catalyst when fresh and when degenerated is also given.

The catalyst used is one of the type described in U.S. Pat. No. 3,882,159. After use for a protracted period in an ammoxidation reactor, the catalyst was heated at 550° C for a period of 2 hours at substantially atmospheric pressure under an atmosphere of air and steam with the partial pressure of steam in the atmosphere maintained at 250 mm.

Three samples of a catalyst representing the three stages in the catalyst life were then used in an ammoxidation reaction using the same reactor which comprised a vertically oriented tubular reactor having a length of 60 cm. and an internal diameter of 1.3 cm. Into this reactor were placed 25 ml. of the catalyst. New catalyst is designated A, degenerated or "spent" catalyst is B, and catalyst regenerated by the process of the invention is C. Moles of oxygen, ammonia and helium in the feed were about 2.1, 1.2 and 7.3 for each mole of propylene.

| Catalyst A | | | | |
|---|---|---|---|---|
| Feed rate (ml/min) | 240 | 240 | 194 | 194 |
| Temperature (° C) | 435 | 435 | 435 | 435 |
| Pressure (atmos.) | 2 | 2 | 2 | 2 |
| Contact Time (sec.) | 2.6 | 2.6 | 3.2 | 3.2 |
| % Propylene Conversion | 94.1 | 92.9 | 95.6 | 94.5 |
| % Acrylonitrile Selectivity | 74.7 | 74.6 | 74.1 | 73.0 |
| % Acrylonitrile Yield | 70.3 | 69.3 | 70.8 | 69.0 |

| Catalyst B | | | |
|---|---|---|---|
| Feed Rate (ml/min) | 214 | 250 | 194 |
| Temperature (° C) | 435 | 435 | 435 |
| Pressure (atmos.) | 2 | 2 | 2 |
| Contact Time (Sec.) | 3.0 | 2.5 | 3.3 |
| % Propylene Conversion | 95.7 | 95.8 | 97.9 |
| % Acrylonitrile Selectivity | 63.5 | 71.0 | 69.4 |
| % Acrylonitrile Yield (on propylene) | 60.8 | 68.0 | 68.0 |

| Catalyst C | | | | | |
|---|---|---|---|---|---|
| Feed Rate (ml/min) | 261 | 261 | 261 | 200 | 180 |
| Temperature (° C) | 440 | 440 | 445 | 445 | 445 |
| Pressure (atmos.) | 2 | 2 | 2 | 2 | 2 |
| Contact Time (Sec.) | 2.4 | 2.4 | 2.4 | 3.1 | 3.5 |
| % Propylene Conversion | 95.2 | 96.1 | 96.7 | 96.5 | 98.4 |
| % Acrylonitrile Selectivity | 78.4 | 77.3 | 77.9 | 79.0 | 75.7 |
| % Acrylonitrile Yield | 74.6 | 74.3 | 75.3 | 76.2 | 74.5 |

Taking the best AN yield for each and giving the corresponding conversion and selectively for each, we have:

A — 70.8, 95.6, 74.1
B — 68.0, 95.8, 71.0
C — 76.2, 96.5, 79.0

Thus it can be seen that regeneration by the process of the invention restores the catalyst to a performance level that is even better than that of fresh catalyst and there is no need for the addition of further components to the catalyst.

EXAMPLE 2

This Example compares the performance of a catalyst having the same composition as described in Example 1 under three sets of conditions.

The reactor used in Example 1 was charged with the catalyst having the same formulation as that used in that Example. A flow of propylene, ammonia and a helium/oxygen mixture to simulate air was established over the catalyst under ammoxidation conditions. The performance of the catalyst when operating at peak efficiency was recorded and is reported in Table 1 below as "Series A."

The catalyst was then artificially degenerated at an accelerated rate by removing the flow of oxygen and propylene and leaving only the helium and ammonia. After 15 minutes of this deactivation, which left the catalyst virtually inactive, the gas flow over the catalyst was changed to one of air plus steam at about atmospheric pressure, the partial pressure of the steam being 250 mm, and the temperature was raised to 550° C, (the regeneration process of the invention). After 2 hours of such treatment the original ammoxidation reactant flow over the catalyst was re-established and the performance of the catalyst was recorded. The results showed that the catalyst had not been fully regenerated and accordingly the regeneration conditions described above were re-established for a further hour. At the end of that time the conditions were changed to those suitable for ammoxidation and the catalyst performance was again recorded, (Series B in Table 1).

The catalyst was then subjected to a treatment in which it was heated in air at 550° C for an hour to simulate conventional regeneration conditions and this catalyst was then used in the same reactor to ammoxidize propylene. It was found that the results (Series C in Table 1) showed a decline in the effectiveness with which the ammonia feed was utilized (i.e. more ammonia was required to produce the same amount of acrylonitrile) and that there had been a slight gain in total conversion of the propylene with a substantial decline in the selectivity to acrylonitrile.

Thus a conventional air regeneration treatment reduced the overall efficiency of the catalyst that had been regenerated by the process of the invention.

molybdenum atoms which comprises heating the catalyst at a temperature of from 400° to 650° C and at a pressure of from 1.0 to 2.0 kg/cm$^2$ in an atmosphere comprising from 20 to 45% by volume of steam, the balance being air or a gas inert to the catalyst under the above conditions, for a period of at least one hour.

2. A process according to claim 1 in which the catalyst is heated at substantially atmospheric pressure.

3. A process according to claim 1 in which the catalyst is heated at substantially atmospheric pressure in the presence of an air/steam mixture wherein the partial pressure of steam in the mixture is from 200-300 mm.

4. A process for the regeneration of an olefin ammoxidation catalyst in which at least 40% of the atoms of the active metallic elements in the catalyst are molybdenum atoms which comprises heating the catalyst composition at substantially atmospheric pressure and a temperature of from 500° to 550° C for a period of 1 to 24 hours under an atmosphere consisting of a mixture of air and steam with a partial pressure of steam of from 200 to 300 mm.

5. A process for the regeneration of an olefin ammoxidation catalyst composition defined by the following

TABLE 1

| | Cat. Vol. (cc) | Press. (atmos) | Temp. °C | Flow cc/mm | Mole Ratio NH$_3$/C$_3$* | Cont. time (sec) | % conv. of C$_3$ | % select. to AN** | % Yield on C$_3$ | % Yield on NH$_3$ |
|---|---|---|---|---|---|---|---|---|---|---|
| Series A | 35 | 2 | 428 | 208 | 1.13 | 4.2 | 99.7 | 72 | 71.8 | 63.5 |
| (Catalyst at optimum | 35 | 2 | 428 | 150 | 1.13 | 5.8 | 99.9 | 71.3 | 71.3 | 63.1 |
| performance level) | 35 | 2 | 428 | 103 | 1.13 | 8.4 | 99.9 | 69.4 | 69.3 | 61.4 |
| Series B | 35 | 2 | 421 | 200 | 1.13 | 4.4 | 99.1 | 69.7 | 69.1 | 61.2 |
| (Regen. by process | 35 | 2 | 429 | 200 | 1.13 | 4.4 | 99.2 | 72.9 | 72.3 | 63.9 |
| of inv.) | 35 | 2 | 430 | 200 | 1.13*** | 4.4 | 99.5 | 72.0 | 71.6 | 63.4 |
| Series C | 27 | 2 | 434 | 208 | 1.30 | 3.2 | 97.4 | 71.7 | 69.8 | 54.0 |
| (Conventional regen.) | 27 | 2 | 430 | 177 | 1.30 | 3.8 | 99.0 | 70.5 | 69.8 | 54.0 |
| | 27 | 2 | 431 | 200 | 1.30 | 3.4 | 98.3 | 70.8 | 69.6 | 53.5 |

*C$_3$ means propylene
**AN means acrylonitrile
***Ratio needed to make propylene selectivity comparable to Series A and B.

The above Examples demonstrate that the regeneration process of the invention results in a catalyst that has greater selectivity to the desired nitrile, (at the expense of a small reduction in total conversion of the hydrocarbon feedstock), then catalyst regenerated by the conventional process and is comparable or better than new, undegenerated catalyst.

The above Examples are for the purpose of illustration only and are not intended to limit the application of the invention. It is anticipated that minor variations could be made in the detailed operation of the processes described without changing the essential concept thereof. It is intended that all such variations be embraced within the purview of this invention. What is claimed is:

1. A process for the regeneration of a spent olefin ammoxidation catalyst in which at least 20% of the atoms of the active metallic elements in the catalyst are formula:

$$Mo_{12}Bi_aFe_bM_mE_eX_xZ_zO_n$$

where M is an alkali metal, E is an alkaline earth metal, X is phosphorus, arsenic or antimony, Z is cobalt or nickel, $a$ and $b$ are from 0.1 to 12, $m$ is 0.1 to 8, $e$ is from 0 to 8, $x$ is from 0 to 6, $z$ is from 0 to 12 and $n$ is a number determined by the valence requirements of the other elements present, $a$, $b$, $m$, $e$, $x$, and $z$ being chosen such that molybdenum provides at least 20% of the atoms of the active metallic element in the catalyst, which process comprises heating the catalyst composition at substantially atmospheric pressure and a temperature of from 500° to 550° C for a period of 1 to 24 hours under an atmosphere consisting of a mixture of air and steam with a partial pressure of steam of from 200 to 300 mm.

* * * * *